United States Patent
Humphrys et al.

(10) Patent No.: US 9,603,536 B2
(45) Date of Patent: Mar. 28, 2017

(54) COMPACT TECHNIQUE FOR VISUALIZATION OF PHYSIOLOGICAL CLINICAL AND BEDSIDE DEVICE DATA USING FISHBONE REPRESENTATION FOR VITALS

(71) Applicant: KONINKLIJKE PHILIPS N.V., Eindhoven (NL)

(72) Inventors: John Francis Humphrys, Needham, MA (US); Youssef Abou-Hawili, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/723,512

(22) Filed: May 28, 2015

(65) Prior Publication Data

US 2015/0257716 A1    Sep. 17, 2015

Related U.S. Application Data

(60) Provisional application No. 62/009,947, filed on Jun. 10, 2014.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0022* (2013.01); *A61B 5/7275* (2013.01);
(Continued)

(58) Field of Classification Search
CPC . A61B 5/02055; A61B 5/0022; A61B 5/7275; A61B 5/742; A61B 5/021;
(Continued)

(56) References Cited

U.S. PATENT DOCUMENTS 8,639,318 B2    1/2014 Hatlestad et al.
9,282,892 B2 *  3/2016 Sohn ........................ A61B 5/00
(Continued)

FOREIGN PATENT DOCUMENTS

WO    2008050323 A2    5/2008

OTHER PUBLICATIONS

Drews, F. A., et al.; Evaluation of a Configural Vital Signs Display for Intensive Care Unit Nurses; 2014; The Journal of the Human Factors and Ergonomics Society; 56(3)569-580.
(Continued)

*Primary Examiner* — Catherine Voorhees (57) ABSTRACT

A patient's vital sign measurements are displayed in a fishbone diagram defined by a horizontal line with a vertical line crossing it to form four compartments. The patient's respiratory rate and heart rate are displayed in assigned compartments above the horizontal line separated by the vertical line and the patient's oxygen saturation (SpO2) and temperature are displayed in assigned compartments below the horizontal line separated by vertical lines. Two diverging horizontal lines form a sideways "V" are connected with the right hand side of the horizontal line to define a fifth compartment in which the patient's blood pressure is displayed.

17 Claims, 5 Drawing Sheets

(51) Int. Cl.
   *A61B 5/1455*   (2006.01)
   *A61B 5/08*     (2006.01)
   *A61B 5/024*    (2006.01)
   *A61B 5/021*    (2006.01)
(52) U.S. Cl.
   CPC .............. *A61B 5/742* (2013.01); *A61B 5/021* (2013.01); *A61B 5/024* (2013.01); *A61B 5/0816* (2013.01); *A61B 5/14551* (2013.01); *A61B 5/746* (2013.01); *G05B 2219/23159* (2013.01); *G05B 2219/23165* (2013.01)
(58) Field of Classification Search
   CPC ... A61B 5/024; A61B 5/0816; A61B 5/14551; A61B 5/746; G05B 2219/23159; G05B 2219/23165
   See application file for complete search history.

(56) References Cited

U.S. PATENT DOCUMENTS

| | | | | |
|---|---|---|---|---|
| 2004/0158132 A1* | 8/2004 | Zaleski | ............... | A61B 5/0002 600/301 |
| 2008/0281168 A1* | 11/2008 | Gibson | ............... | A61B 5/0205 600/301 |
| 2009/0054743 A1 | 2/2009 | Stewart | | |
| 2010/0177100 A1 | 7/2010 | Carnes et al. | | |
| 2010/0280333 A1* | 11/2010 | Parshuram | ......... | G06F 19/3418 600/301 |
| 2011/0054335 A1* | 3/2011 | Zhang | ............... | A61B 5/0452 600/509 |
| 2013/0267793 A1* | 10/2013 | Meador | ............... | A61B 5/0205 600/301 |

OTHER PUBLICATIONS

EMS Field Bridge Version 5.1 Release Notes; Image Trend; http://www.msdh.state.ms.us/msdhsite/index.cfm/47,4854,309,pdf/FieldBridge51ReleaseNotes.pdf accessed May 20, 2014.

* cited by examiner

COMPACT TECHNIQUE FOR VISUALIZATION OF PHYSIOLOGICAL CLINICAL AND BEDSIDE DEVICE DATA USING FISHBONE REPRESENTATION FOR VITALS

CROSS REFERENCE TO RELATED APPLICATIONS

This application claims the benefit of U.S. provisional application Ser. No. 61/009,947 filed Jun. 10, 2014, which is incorporated herein by reference.

The present application relates generally to patient care systems for presenting information to facilitate speed and accuracy of patient medical information. It finds particular application in conjunction with nursing and physician care of a patient and patient monitoring and will described with particular reference thereto. However, it is to be understood that it also finds application in other usage scenarios and is not necessarily limited to the aforementioned application.

In a clinical care unit, patient vital signs and other physiological measurements and assessments are performed on a routine basis. The frequency for checking and measuring patient vital signs varies from patient to patient and may be continuous, every 30 minutes, another time span, a variable time span or the like. A patient's vital signs are often measured using a continuous monitor or a member of the medical staff performs the routine vital sign measurements. Vital signs include blood pressure, temperature, heart rate, respiration rate, and $SpO_2$. As vital signs and measurements are taken, the information is entered into the patient's medical file. The results are then made available for review by the caregiver and the patient's physician.

During a patient's stay in a clinical care unit, a patient may require differing levels of care. For example, upon being admitted, a patient may require more continuous care and then can be stepped down to less around the clock care. However, one factor in determining whether a patient is ready to step down or to be released, is how stable a patient's vital sign measurements are. In a clinical care unit, a caregiver is typically responsible for a plurality of patients at a given time. The location of vital signs varies from monitor to monitor. Moreover, some monitors allow different amounts of information to be displayed for each patient or to change the amount of information for a given patient. When the amount of information changes, the location of some vital signs and other medical information on the display changes in order to fit more or less information into the assigned display window.

Due to the increasing number of patients there is a need for quicker and easier access to a patient's medical information, particularly easier to read vital signs. It has become not only important that patient vital information is readily available but also that it is displayed in a consistent manner.

The present application provides new and improved methods, which overcome the above-referenced problems and others.

The present application proposes to use a fishbone pattern with specified compartments assigned to specific vital signs to standardize vital sign reporting for easier readability. The use of easy to access and read patient information improves clinical productivity and patient care and facilitates clinician review to determine if the vitals are within normal limits or abnormal.

In accordance with one aspect, a method for displaying a patient's vital sign measurements is provided. A horizontal line with one or more vertical crossing lines is displayed to define four or more compartments. The patient's respiratory rate, heart rate, blood oxygen saturation, and temperature are each displayed in an assigned one of the compartments. Two divergent lines forming a sideways "V" are connected with a right hand side of the horizontal line to define another compartment. The patient's blood pressure is displayed in the another defined compartment defined by the two diverging lines.

In accordance with another aspect, a patient vital sign monitoring and display system is provided. One or more physiological sensors measure the patient's vital signs. An input/output circuit communicates with a communication network. One or more processors are connected with the sensors, the input/output circuit, and the display device and are configured to control the display device to generate a fishbone diagram defining a plurality of compartments and display patient vital sign measurements each in a consistent compartment of the fishbone diagram.

In accordance with another aspect, a patient vital sign monitoring and display system includes one or more processors. The processors are configured to receive vital sign measurements including a respiration rate measurement, a heart rate measurement, an SpO2 measurement, and a temperature measurement. The one or more processors control a display device to generate a fishbone diagram including a horizontal line, a vertical line crossing the horizontal line to define a first display area above the line and to the left of the vertical line, a second display area above the horizontal line and to the right of the vertical line, a third display area below the horizontal line and to the left of the vertical line, and a fourth display area below the horizontal line and to the right of the vertical line. The one or more processors further control the display to display each of the respiration rate measurement, the heart rate measurement, the SpO2 measurement, and the temperature measurement, without identifying labels, in an assigned one of the display areas consistently across a patient population.

One advantage resides in improved readability of patient vital sign information.

Another advantage resides in improved availability of the patient vital sign information.

Another advantage resides in improved clinical workflow.

Another advantage resides in improved patient care.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

The present application is directed to a method and apparatus for displaying and laying out patient's vital sign information on a caregiver display. The present disclosure is inspired by the insight that current displays for reviewing patient vital sign measurements are inconsistently laid out and require significant display space, resulting in slower data interpretation and decreased accuracy of data interpretation by clinical caregivers. Currently, fishbone diagrams are used in reporting lab results. This placement of laboratory results in the diagram is consistent between labs and hospitals resulting in quick and easy to read lab reports. The use of a similar layout for patient vital information will allow faster data interpretation, consistency among data reports, and improved patient care.

The present application is further directed to a caregiver display incorporating and displaying the patient's vital sign information in a consistent readable display format.

Figure 1:
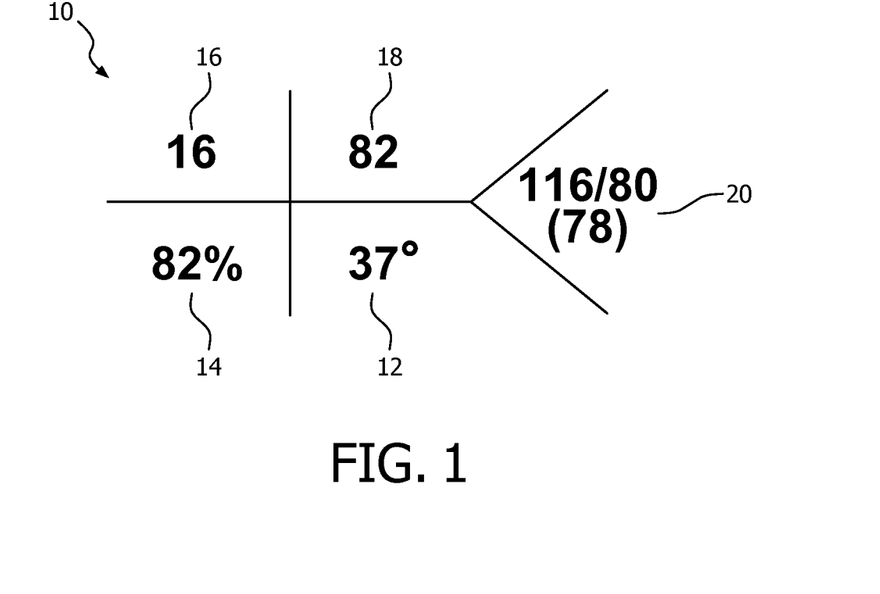
FIG. 1 diagrammatically displays a patient's vital signs using a fishbone diagram.

With reference to FIG. 1, a consistent and simplified layout for displaying patient vital sign measurements is shown. The layout includes a fishbone diagram 10, such as is commonly used in reporting lab results in the medical field, which includes a horizontal line and an intersecting vertical line which subdivides and defines four vital signs compartments. Each compartment contains one vital sign measurement. Extending to the right of the four compartments is a fifth compartment defined by two diverging horizontal lines to form a sideways "V". The most commonly used and checked vital signs include respiratory rate 16, heart rate 18, blood oxygen saturation 14, temperature 12, and blood pressure 20. The rate vital sign measurements (respiration rate and heart rate) are displayed in the top compartments while a patient's blood oxygen saturation and temperature vital sign measurement are displayed in the bottom compartments. By consistently standardizing the location of the vital sign measurements in the fishbone diagram, the labels explaining each value can be eliminated and less space is required to display all vital sign measurement values. A typical heart rate is 70 to 80 beats per minute while a typical respiration rate is 15-16 breaths per minute, therefore, labels are not needed to differentiate between the rate measurements in the top compartments. Additionally, a patient's blood oxygen saturation (SpO$_2$) and temperature are displayed with the % and ° labels therefore further reducing the need to label the vital sign measurements. The conventional way for displaying a patient's blood pressure differentiates the blood pressure vital sign measurement from the other vital signs. A patient's blood pressure measurement is displayed to the right of the other vital sign measurements 20 in the fifth compartment.

Figure 2:
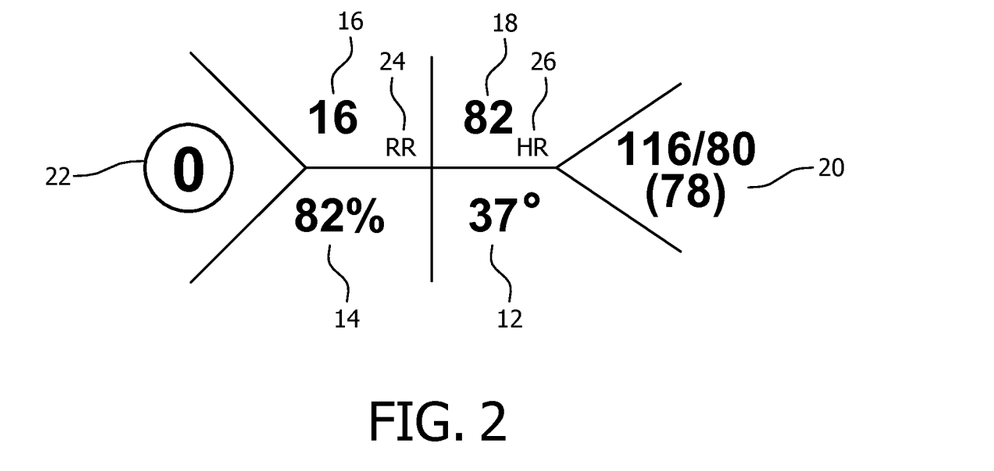
FIG. 2 diagrammatically displays another example of displaying vital signs using a fishbone diagram where one of the pieces of information is calculated from the patient's vital signs.

In the embodiment of FIG. 2, a sixth compartment formed by two diverging horizontal lines to form a sideways "V" is displayed to the left of the other vital sign measurements 22. The sixth measurement in the embodiment of FIG. 2 is a patient's early detection index or warning score (EWS) or modified early warning score (MEWS), which is calculated from the patient's other vital sign measurements 12, 14, 16, 18, 20. As discussed above, labeling the vital sign measurements is not necessary. However, labels 24, 26 for the rate vital signs can be included.

Figure 3:
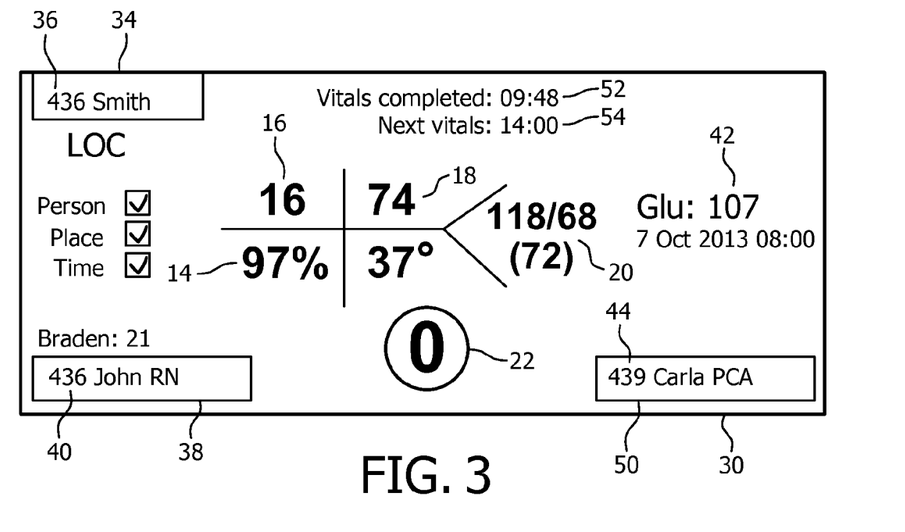
FIG. 3 diagrammatically displays a fishbone diagram as an element of a display of the patient's vital signs on a caregiver display.
Figure 4:
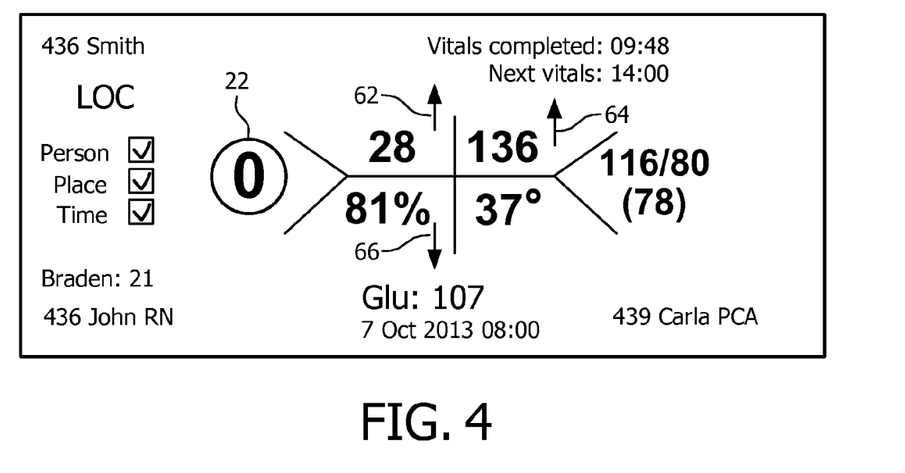
FIG. 4 diagrammatically displays a fishbone diagram with a patient's vital sign information with two vitals out of range.

The fishbone diagram 10 and the vital signs can be displayed as a unit when other information is added. By maintaining the above discussed relationship between the fishbone diagram and vital sign values, the meaning of the displayed values is clear regardless where the fishbone diagram is placed among the other information. FIG. 3 illustrates an example of a caregiver display with the patient's vital sign measurements included in the fishbone pattern as part of the display. Information about the patient is included in a display 30. Each display 30 includes a patient name 34 and patient location 36 in a common location such as the upper left corner. Each display 30 includes a name of a nurse 38 currently assigned to the patient and a current location 40 of the nurse as received by a location unit. Each display 30 can also include a name of an aide 44 assigned to the patient and the current location 50 of the aide as received by the location unit. The use of the consistent and space saving fishbone vital sign display allows additional patient information to be easily read or displayed on the display 30 unit. Each display can include the early detection index 22 as calculated by the scoring unit based on the last vital signs at the bottom of the display 30 or as part of the six compartment fishbone diagram as seen in FIG. 4.

Patient vital signs are taken on a routine basis. As such, it is important for the caregiver to quickly understand when the last vital signs were taken and when the next vital sign measurements are to be taken. The display unit includes a time of last completion 52 and a next scheduled time to be completed 54. Completed patient assessments and/or measurements include the values and/or indications of completion. Each completed measurement of the patient vital signs includes a value such as the temperature 12, the SpO$_2$ level 14, the respiration rate 16, the heart rate 18, the blood pressure 20, and the like. The display can also include a glucose level 42 or other measurement.

In addition to the displayed vital sign values measurements, other information concerning the vital sign measurements can be displayed offering more information about the status of a patient's vital sign measurement. In clinical care, it is important to not only monitor and measure a patient's vital signs but to also monitor whether the measured values are within a normal range for that vital sign. With reference to FIG. 4, arrows 62, 64, 66 are displayed next to the vital sign information indicating whether a given value is in or out of range. An arrow pointing upward 62, 64 indicates that the patient's vital sign is higher than the normal range while an arrow pointing down 66 indicates that the patient's vital sign is lower than the normal range.

The length of the shaft of the arrow and the color of the arrow also offers information concerning the patient's vital sign status. The color of the arrow indicates the severity of the alarm. The system can be programmed to alert appropriate clinical care staff that a vital sign is out of range. Multiple levels of alerts and different out of range sensitivities can be programmed depending upon the vital sign and/or the patient. When a vital sign is out range, the arrow head is colored to indicate the severity of the alarm. For example, an infant will have a higher respiratory rate than an adult and the system can be adjusted to reflect whether the vital sign values are out of range accordingly. When a vital sign is only moderately out of range, the arrow head may be one color such as yellow and when a vital sign is significantly out of range, the arrow head may be colored a secondary color such as red. Various other types of color-coding can be included such as color-coding the number values or the background. The length of the arrow shaft is an indication of a worsening condition over time. For example, a yellow arrowhead without a shaft indicates a new alarm. An arrowhead with a shaft indicates that the alarm was tending in a particular direction for a longer period of time.

If a patient's heart rate continues to drop out of range, the length of the arrow shaft will continue to lengthen. The longer the shaft of the arrow, the longer the alarm has been out of range.

Figure 5:
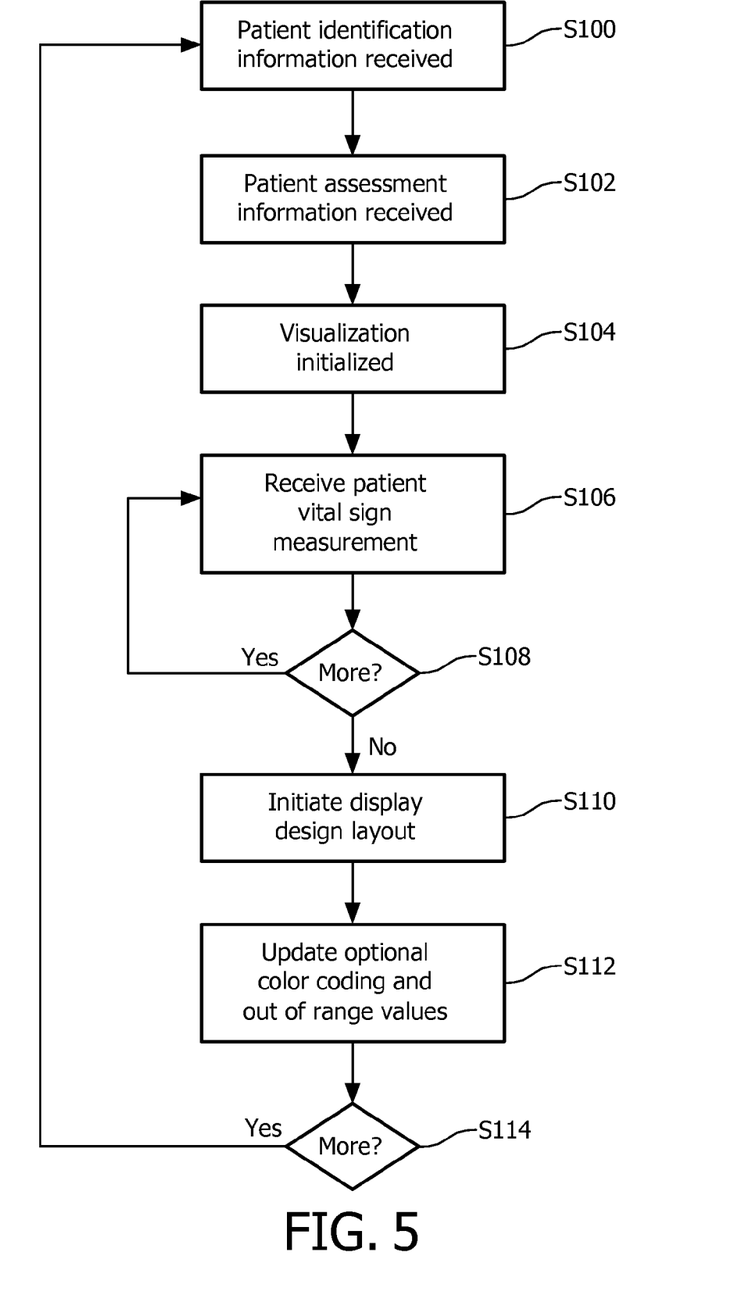
FIG. 5 illustrates a method flow chart or means for determining the patient information to display and for laying the information out on the caregiver display.

FIG. 5 illustrates the method of acquiring patient vital sign information and displaying the information in a consistent manner on the patient display 30. In a step S100, patient names and locations are received and associated with a corresponding display. A system identifies and tracks patient assessment and patient vital signs for each patient according to the schedules for each patient in a step S102. For each patient, each assessment and each measurement of a vital sign or other measurement is identified and scheduled. The system creates events for assessment and/or measurements. The system tracks the last completed assessment and/or measurement and the next scheduled assessment and/or measurement. The system visualizes the identified and tracked assessment and measurements grouped for each patient in a consistent format such as a sector. The system includes one or more computer processors or controllers which are programmed or configured to perform these steps.

The display device 30 displays the visualization of the vital signs fishbone and other information in a step S104. The visualization defines and lays out the patient vital sign measurements. After taking a patient's vital sign measurement, the information is input into the one or more computer processors to be used to control the display device. In a step S106, the system receives the patient's vital sign measurements. As each vital sign measurement is received, the system classifies each input as the given type of vital sign measurement. The vital signs can be manually measured and input or electronically sensed and input or a combination thereof. At step S108, the system checks if more vital signs are needed or entered. If so, the system checks for receipt of additional patient vital sign measurements at S106. If no additional vital signs are received or needed, the system displays the most recent vital signs or other medical information on the display at a step S110. Based upon the classification previously performed by the system at step S106, the one or more processors of the system controls the display to display the fishbone diagram on the display device 30. Each vital sign measurement is added to the pre-assigned compartment of the fishbone diagram. If color coding or arrows are to be added, at a step S112, the system controls the display to add the appropriate color coding and arrows based upon user programmed range values for each vital sign measurement. At a step S114, the system repeats the method to check if vital signs need to be updated again for a given patient or to begin updating new patient's vital sign measurements.

Figure 6:
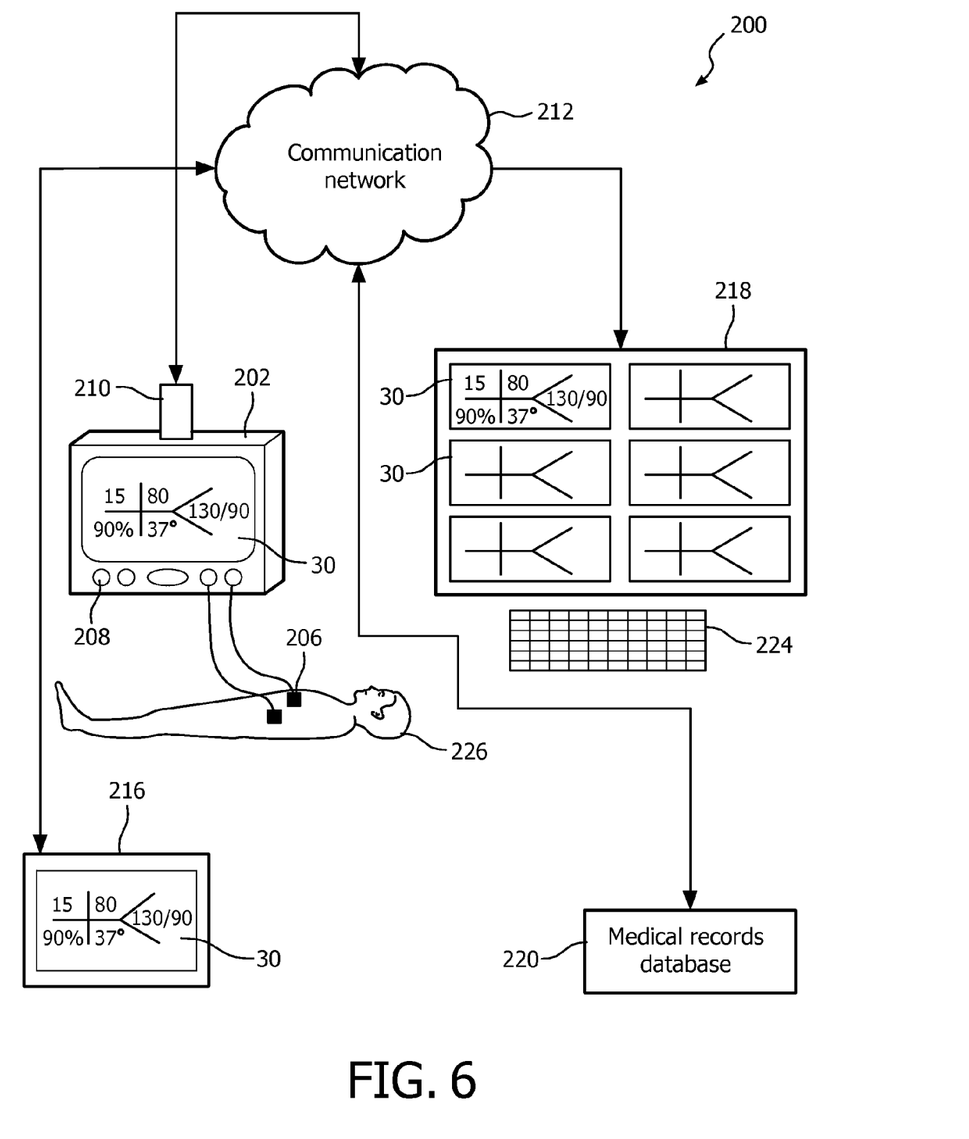
FIG. 6 illustrates a block diagram of a system infrastructure of a medical institution according to aspects of the present application.

FIG. 6 illustrates a patient monitoring system 200. A bedside monitor 202 which houses the display 30 and one or more processors which are connected with the display 30, physiological parameter sensors 206 connected to a patient 226 or a user input device 208. An input/output circuit 210 communicates with a communications network 212 such as one or more of the Internet, Intranet, a local area network, a wide area network, a wireless network, a wired network, a cellular network, a data bus, and the like. It should also be appreciated that the components of the IT infrastructure be located at a central location or at multiple remote locations.

The bedside monitor communicates via the communications network 212 with a medical records database 220 which stores the vital signs, medical history, and other patient and medical information from the bedside monitor 202. The bedside monitor 202 can also retrieve medication information from the medical records database 220. The display 30 is sent to the clinician's PDA 216 and/or to a central display 218. The central display 218 is located in a common area of the hospital such as a nurse's station, on the wall of a ward or unit, or the like and contains the displays 30 for each of a plurality of patients located in the ward or unit. A nurse or clinician can see all of the patient's vital signs concurrently. Uniformity of the vital signs presentation in the fishbone 10 facilitates review of the vital signs of the plurality of patients. Optionally, a user input device 224 is provided to allow a user to manually input patient vital sign information.

Figure 7:
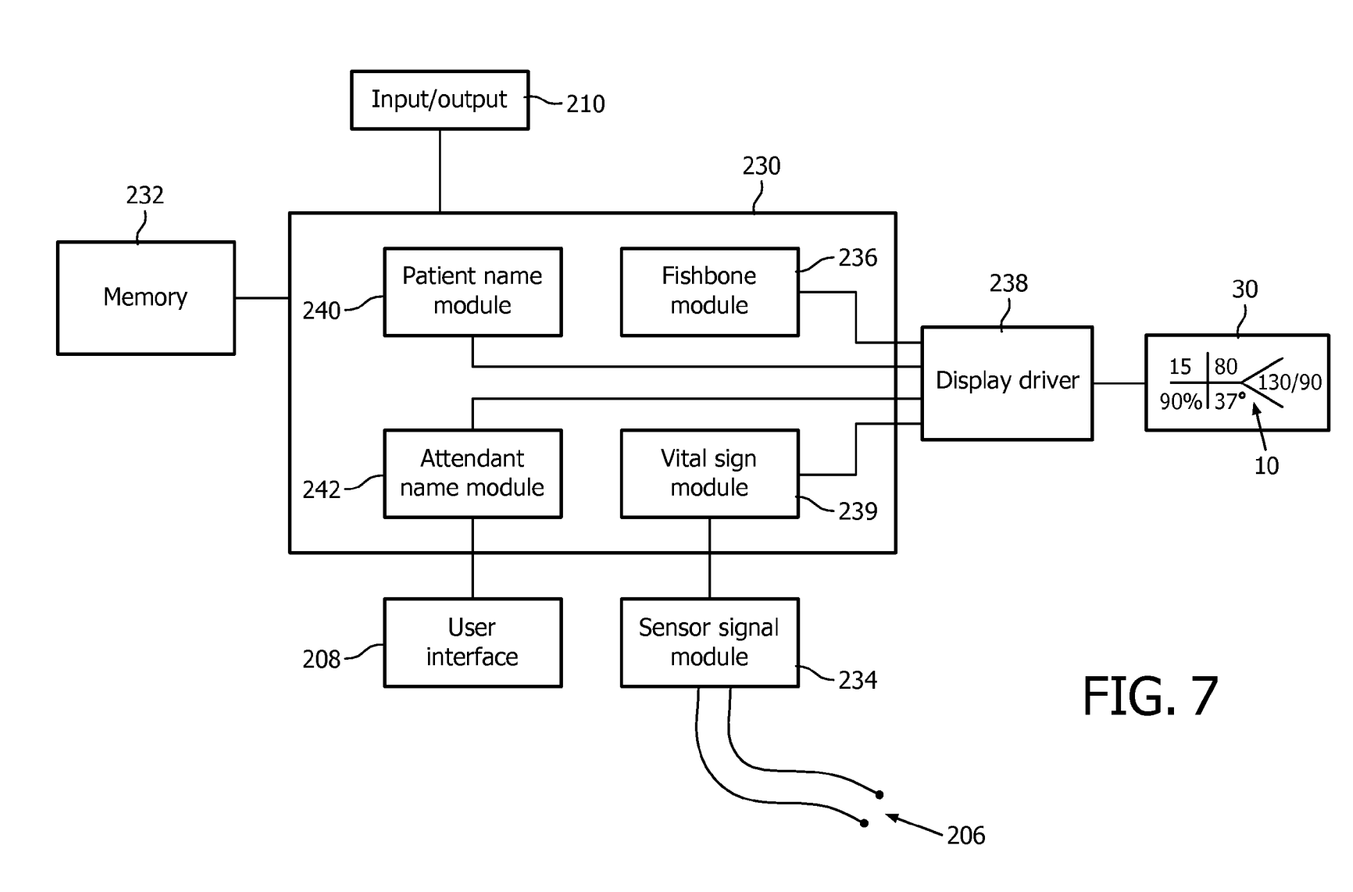
FIG. 7 illustrates a block diagram of a bedside monitor.

With reference to FIG. 7, the bedside monitor 202 includes one or more computer processors 230 which include a non-transitory computer readable memory 232 which carries software to control the processor to perform the method of FIG. 5. A sensor signal processor 234 converts the signals from the sensors into appropriate form and format to be processed by the one or more processors 230. The one or more processors include a fishbone module 236 which controls a display driver 238 to generate the fishbone 10 on the display 30. A vital signs module 239 provides the display driver with the values of the vital signs to be displayed in each compartment of the fishbone. A patient name module 240, an attending clinician module 242, and other modules (not shown) supply the display driver with the appropriate patient name, attending clinician name, and the other information to be display on the display 30. See, for example, FIG. 3 or 4. Patient name information and attending clinician name information can be input through the user interface 208 on the bedside monitor, e.g., buttons, keys, or a touch screen, or the like, or through the input/output network 210 via the communications network.

The invention has been described with reference to the preferred embodiments. Obviously, modifications and alterations will occur to others upon reading and understanding the proceeding detailed description. It is intended that the invention be construed as including all such modifications and alterations insofar as they come within the scope of the appended claims or the equivalents thereof.

The invention claimed is:

1. A method for displaying a patient's vital sign measurements, comprising:
   displaying a horizontal line with one or more vertical crossing lines to define four or more compartments;
   displaying the patient's respiratory rate, heart rate, blood oxygen saturation, and temperature, each in an assigned one of the compartments;
   displaying two diverging lines forming a sideways "V" connected with a right hand side of the horizontal line to define another compartment;
   displaying the patient's blood pressure in the compartment defined by the two diverging lines;
   calculating an early detection index form the patient's vital sign measurements;
   displaying a second two diverging lines forming a sideways "V" connected with a left hand side of the horizontal line to define a further compartment; and
   displaying the early detection index in the further compartment defined by the second two diverging lines.

2. The method for displaying a patient's vital sign measurement according to claim 1, wherein the patient's respiratory rate and heart rate are displayed in the compartments above the horizontal line and the patient's blood oxygen saturation, and temperature are displayed in the compartments below the horizontal line.

3. The method for displaying a patient's vital sign measurement according to claim 1, wherein an upward or downward pointing arrow is displayed in one or more of the compartments to indicate that a vital sign measurement displayed in the compartment is out of range.

4. The method for displaying a patient's vital sign measurement according to claim 3, wherein
the arrow pointing downward indicates a vital sign value below a low limit, and
the arrow pointing upward indicates a vital sign value that is above a high limit.

5. The method for displaying a patient's vital sign measurement according to claim 3, wherein the arrow is color coded to indicate a severity of how far a patient vital sign is above or below a defined alarm limit.

6. The method for displaying a patient's vital sign measurement according to claim 1, wherein the patient's respiration rate is displayed in the compartment above the horizontal line and to the left of the vertical line and the patient's heart rate is displayed in the compartment that is above the horizontal line and to the right of the vertical line.

7. The method for displaying a patient's vital sign measurement according to claim 1, wherein the patient's blood oxygen saturation is displayed in the compartment below the horizontal line and to the left of the vertical line and the patient's temperature is displayed in the compartment that is below the horizontal line and to the right of the vertical line.

8. A non-transitory computer-readable storage medium carrying software which controls one or more electronic data processing devices to control a display device to perform the method according to claim 1.

9. A patient vital sign device comprising:
one or more sensors which measure the patient's vital signs;
a display device; and
one or more electronic data processing devices connected with the sensors and the display device and configured to control the display device to perform the method according to claim 1.

10. The patient vital sign monitoring and display system according to claim 9, wherein the display device is in at least one of: a computer, a smart phone device, a web-enabled watch with a display face, a wearable electronic display, a PDA, a bedside monitor, and a video display screen.

11. A method for displaying a patient's vital sign measurements, comprising:
displaying a horizontal line with one or more vertical crossing lines to define four or more compartments;
displaying the patient's respiratory rate, heart rate, blood oxygen saturation, and temperature, each in an assigned one of the compartments;
displaying two diverging lines forming a sideways "V" connected with a right hand side of the horizontal line to define another compartment; and
displaying the patient's blood pressure in the compartment defined by the two diverging lines, wherein an upward or downward pointing arrow is displayed in one or more of the compartments to indicate that a vital sign measurement displayed in the compartment is out of range, and wherein a length of the arrow shaft indicates a worsening condition of the vital sign over time.

12. A patient vital sign monitoring and display system comprising:
an input/output circuit configured to communicate with a communication network;
a display device; and
one or more computer processors connected with the input/output circuit and the display device wherein the one or more computer processors are configured to control the display device to generate a fishbone diagram defining a plurality of compartments and display patient vital sign measurements received from the input/output circuit or optionally from a user input device or from one or more physiological parameter sensors configured to measure a patient's vital signs each in a consistent compartment of the fishbone diagram, wherein the one or more processors are further configured to:
determine when a vital sign measurement is above a preselected high limit or below a preselected low limit;
control the display device to display an upward arrow adjacent a vital sign measurement that is above the high limit and a downward arrow adjacent a vital sign measurement that is below the low limit and wherein the arrow has a length to indicate a time measurement of how long a vital signs is above or below a defined alarm limit or color to indicate how far the measured vital sign measurement is above or below the defined alarm limit.

13. The patient vital sign monitoring and display system according to claim 12, wherein the one or more computer processors is further configured to calculate an early detection index from the patient's vital signs and control the display device to display the early detection index.

14. The patient vital sign monitoring and display system according to claim 12, wherein the fishbone diagram includes:
a horizontal line;
a vertical line intersecting the horizontal line to define four compartments; and
a sideways "V" connected with one end of the horizontal line to define a fifth compartment.

15. The patient vital sign monitoring and display system according to claim 14, wherein the one or more processors are further configured to control the display device to display:
a respiration rate measurement in a one of the compartments above the horizontal line and to the left of the vertical line;
a heart rate measurement in a one of the compartments above the horizontal line and to the right of the vertical line;
an SpO2 measurement in a one of the compartments below the horizontal line and to the left of the vertical line; and
a temperature measurement in a one of the compartments below the horizontal line and to the right of the vertical line.

16. The patient vital sign monitoring and display system according to claim 14, wherein one or more processors are further configured to control the display device to display a blood pressure measurement in the fifth compartment.

17. A patient vital sign monitoring and display system comprising:
one or more processors configured to:
receive vital sign measurements including a respiration rate measurement, a heart rate measurement, an SpO2 measurement, and a temperature measurement;
determine when a vital sign measurement is above a preselected high limit or below a preselected low limit;
control a display device to generate a fishbone diagram including a horizontal line, a vertical line crossing the horizontal line to define a first display area above the horizontal line and left of the vertical line, a second display area above the horizontal line and right of the vertical line, a third display area below the horizontal line and left of the vertical line, and a fourth display area below the horizontal line and right of the vertical line, and to display each of the respiration rate measurement the heart rate measurement, the SpO2 measurement, and the temperature measurement without identifying labels in an assigned one of the display areas consistently across a patient population and to display an upward arrow adjacent a vital sign measurement that is above the high limit and a downward arrow adjacent a vital sign measurement that is below the low limit and wherein the arrow has a length to indicate a time measurement of how long a vital sign is above or below a defined alarm limit or color to indicate how far the measured vital sign measurement is above or below the defined alarm limit.

* * * * *